US00PP30987P2

(12) United States Plant Patent
Freyre et al.

(10) Patent No.: US PP30,987 P2
(45) Date of Patent: Oct. 29, 2019

(54) ***RUELLIA* PLANT NAMED 'R16-1-1'**

(50) Latin Name: *Ruellia simplex*
Varietal Denomination: R16-1-1

(71) Applicant: Florida Foundation Seed Producers, Inc., Marianna, FL (US)

(72) Inventors: Rosanna Freyre, Gainesville, FL (US); Victor Zayas, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 15/932,771

(22) Filed: Apr. 23, 2018

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1
CPC ..... A01H 5/02
See application file for complete search history.

*Primary Examiner* — Keith O. Robinson
(74) *Attorney, Agent, or Firm* — Koenig IP Works, PLLC

(57) ABSTRACT

'R16-1-1' is a new *Ruellia simplex* plant distinguished by having excellent performance under partial sun and in containers, medium-sized red-purple flowers with a darker red-purple corolla tube, maximum plant height at 49 cm, profuse branching, and no fruit production, as disclosed.

2 Drawing Sheets

ACKNOWLEDGMENT OF FEDERAL RESEARCH SUPPORT

This invention was made with government support under FLA-ENH-005388 awarded by the National Institute of Food and Agriculture, USDA. The government has certain rights in the invention.

Genus and species: *Ruellia simplex.*

Cultivar denomination: 'R16-1-1'.

CROSS-REFERENCE TO RELATED APPLICATION n/a

BACKGROUND OF THE NEW CULTIVAR

The invention relates to a new and distinct variety of *Ruellia simplex* plant named 'R16-1-1'. 'R16-1-1' is an $F_1$ seedling from a manual hybridization conducted on Feb. 15, 2015, at the Environmental Horticulture Research Greenhouses (EHRG), University of Florida (UF) in Gainesville, Fla., between female parent 'R14-4x-PK1' (UF proprietary clone, not patented; tetraploid, red-purple flowers) x male parent 'R14-2x-PK1' (UF proprietary clone, not patented; diploid, red-purple flowers). Ploidy level determinations were done by flow cytometry at UF using wild *R. simplex* as a diploid (2n=2x=34) control and 'Purple Showers' (commercial cultivar, not patented) as a tetraploid control. 'R16-1-1' is below the diploid level, so it appears to be an aneuploid, originated from haploid parthogenesis in the tetraploid material parent and had loss of one or more chromosomes (2n=2x−?=34−?).

'R16-1-1' has been reproduced asexually for over one year through vegetative cuttings (stem tip cuttings) and has been shown to retain its distinctive characteristics through successive asexual propagations.

'R16-1-1' has not been made publicly available more than one year prior to the filing date of this application.

SUMMARY OF THE INVENTION

The following are the most outstanding and distinguishing characteristics of 'R16-1-1' when grown under normal horticultural practices in Florida.

1. Excellent performance under partial sun environments and in containers;
2. Medium-sized red-purple flowers with a darker red-purple corolla tube;
3. Average plant height of 49 cm;
4. Profuse branching; and
5. No fruit production.

DESCRIPTION OF THE FIGURES

This new *Ruellia simplex* variety 'R16-1-1' is illustrated by the accompanying photographs which show the plant's form and foliage. The colors shown are as true as can be reasonably obtained by conventional photographic procedures. The photographs were taken from seven-week old plants grown at the EHRG, UF, Gainesville, Fla.

DETAILED BOTANICAL DESCRIPTION OF THE CULTIVAR

Figure 1:
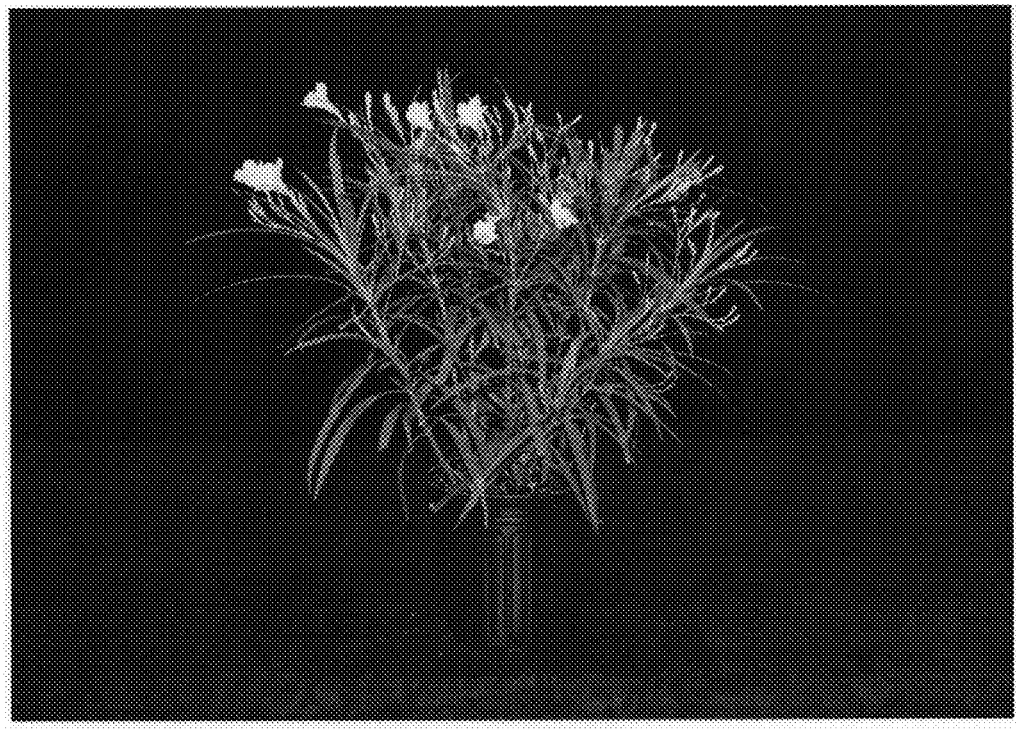
FIG. 1 shows a single plant of *Ruellia simplex* 'R16-1-1' in a one-gallon container, taken on Sep. 14, 2017, at the EHRG, UF, Gainesville, Fla.
Figure 2:
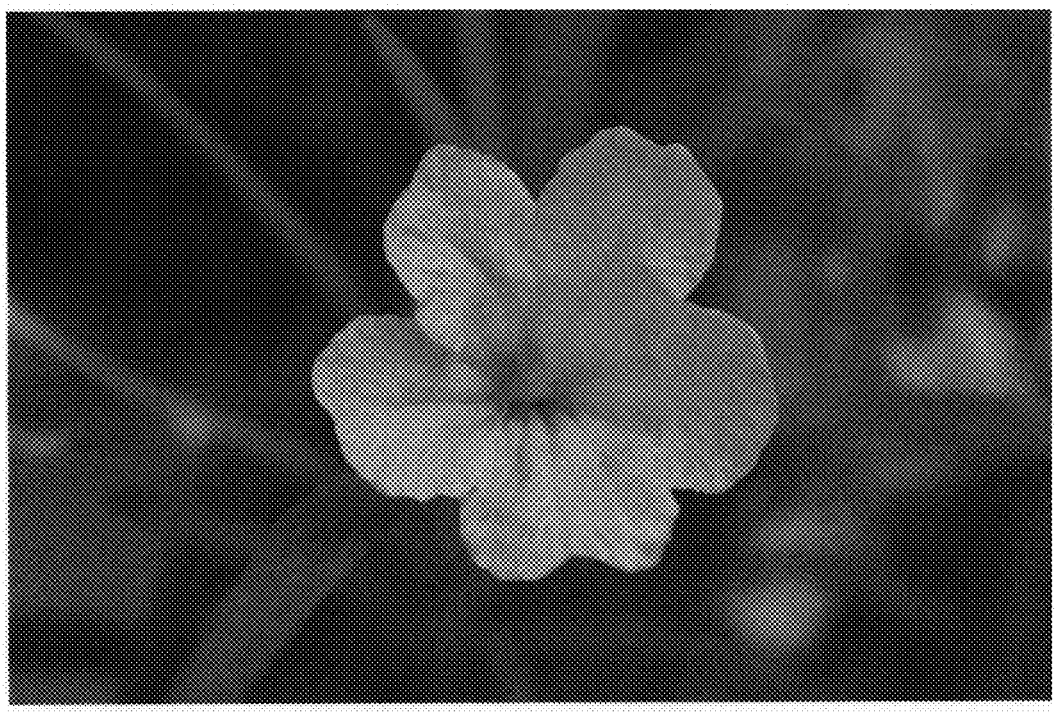
FIG. 2 shows a close-up view of a flower of *Ruellia simplex* 'R16-1-1' taken on Sep. 14, 2017, at the EHRG, UF, Gainesville, Fla.

The following detailed description sets forth the distinctive characteristics of 'R16-1-1'. Plants were propagated by vegetative cuttings on June 2016, and grown in the EHRG, UF, Gainesville, Fla. Plants were approximately seven weeks of age when plant parts were measured and descriptions of color were determined. Color references are to The R.H.S. Colour Chart of The Royal Horticultural Society of London (R.H.S.), 2001 Edition.

BOTANICAL DESCRIPTION

Botanical classification:

*Family*.—Acanthaceae.

*Botanical name*.—*Ruellia simplex*.

*Common name*.—*Ruellia* (*Ruellia*) or Mexican petunia.

*Variety name*.—'R16-1-1'.

Plant description:

*Form*.—Erect.

*Habit*.—Clumping.

*Height* (*from top of soil*).—47-51 cm.

*Width* (*horizontal plant diameter*).—49-53 cm.

Propagation:

*Type*.—Vegetative meristems having at least two nodes.

*Time to initiate roots*.—7 days.

*Time to produce a rooted cutting*.—14 days.

*Root habit*.—Adventitious (fibrous).

*Root description*.—Callus forms in 4-5 days, roots initiate in 7 days and become a highly branched cutting in 14-21 days.

Branches:

*Quantity per plant*.—Approximately 55 when not pinched.

*Branch color*.—RHS 148A (yellow-green) with RHS 187B tint (greyed-purple) when mature. New growth is lighter in color (RHS 138B) and gets darker with light exposure.

*Texture*.—Smooth.

*Pubescence*.—Slightly tomentose, especially at nodes, RHS 155D (white).

*Stem description*.—Round to square shaped stem, 2.0-3.0 cm in diameter at the soil line.

*Branch diameter*.—1.0 cm at the base of a 40-cm-long branch.

*Branch length*.—45-60 cm.

*Internode length*.—1-5 cm.

*Anthocyanin*.—RHS 183B (greyed-purple).

Leaves:

*Quantity of leaves per branch*.—Approximately 50 on a 45-cm branch.

*Arrangement*.—Decussate (opposite pairs).

*Fragrance*.—None.

*Shape*.—Lanceolate.

*Length*.—14-18 cm.

*Width*.—1.3-1.7 cm.

*Apex*.—Narrowly acute.

*Base*.—Attenuate.

*Margin*.—Entire.

*Leaf texture* (*both surfaces*).—Slightly coriaceous.

*Venation color*.—Upper surface: RHS 145B (green). Lower surface: RHS 145C (green).

*Venation pattern*.—Pinnate.

*Color, mature and immature leaf*.—Upper surface: RHS 147A (green) immature, RHS 147A (green) mature. Lower surface: RHS 147B (green) immature, RHS 147A (green) mature.

*Petiole length*.—2-3 cm.

*Petiole diameter*.—0.5 cm.

*Petiole color*.—RHS 146B (yellow-green).

Flowers and seeds:

*Flower*.—Arrangement: Axillary in solitary or several-flowered cyme. Aspect: Actinomorphic corolla with five rounded petals, funnel form. Flowering habit (length of flowering season): April to October (north Florida). Number of inflorescences per plant: 4-8 cymes with 20-40 flowers plus buds. Fragrance: Very mild and slightly sweet. Lastingness of individual bloom: 1 day. Rate of opening: Daily.

*Flower bud*.—Shape: Elliptic. Length: 2.0 cm. Diameter: 0.4 cm. Color: RHS 150B (yellow-green), lower surface RHS 72A (red-purple). Texture: Smooth.

*Corolla*.—Arrangement: Actinomorphic salverform (funnel). Length: 5.3-6.0 cm. Diameter: 3.0-4.0 cm. Color: Upper surface: RHS 73D (red-purple). Lower surface: RHS 73D (red-purple). Texture: Rugose.

*Corolla tube*.—Length: 3.0 cm. Diameter: 1.0 cm. Color: RHS 72A (red-purple), includes bottom of lower petal.

*Banner*.—Not present.

*Keel*.—Not present.

*Calyx*.—Number of sepals per flower: 5. Length: 1.0-1.5 cm. Diameter: 0.5 cm. Apex: Narrowly acute. Base: Fused. Texture (both surfaces): Smooth to glandular. Pubescence: Present (glandular trichomes). Sepal color: Upper surface: RHS 143A (green). Lower surface: RHS 143A (green).

*Pedicels*.—Angle: 15-25°. Length: 1.5-2.0 cm. Diameter: 0.2 cm. Texture: Smooth to glandular (glandular trichomes). Color: Upper surface: RHS 79A (greyed-purple) under full sun, RHS 143B (green) in partial sun. Lower surface: RHS 143B (green).

Reproductive organs:

*Stamens*.—Number: 4 fused to the base of the corolla. Filaments: 4. Color: RHS 155D (white). Length: Two at 2.3 cm, two at 2.6 cm. Diameter: 0.1 cm. Anther color: RHS 155D (white). Pollen amount: Sparse, 12% stainability with lactophenol aniline blue. Pollen color: RHS 155D (white).

*Pistils*.—Number per flower: 1. Pistil length: 2.5 cm. Stigma: Color: RHS 155D (white). Shape: Bilabial and slightly recurved. Length: 0.3 cm. Diameter: 0.2 cm. Style: Color: RHS 155D (white). Length: 2.0 cm. Diameter: 0.1 cm. Ovary: Shape: Hypogenous, elliptic. Color: RHS 143A (green). Length: 0.5 cm. Width: 0.1 cm.

Fruit/seed set: None observed.

Disease and insect resistance: Disease and insect resistance is typical of the species, thus no claims are made of any superior disease or insect resistance with this cultivar. The most common insect pests observed on this cultivar, particularly under greenhouse conditions in Gainesville, Fla., have been mealybugs (*Pseudococcidae*), spider mites (*Tetranychidae*), and aphids (*Aphidoidea*). No susceptibility to any particular pathogens has been observed on this cultivar.

COMPARISON WITH KNOWN CULTIVARS

When 'R16-1-1' is compared to the female parent 'R14-4x-PK1', 'R16-1-1' has shorter plant height and smaller red-purple flowers with a darker red-purple corolla tube, while 'R14-4x-PK1' has tall plant height, and larger red-purple flowers with a darker red-purple corolla tube. When 'R16-1-1' is compared to the male parent 'R14-2x-PK1', 'R16-1-1' has shorter plant height and smaller red-purple flowers with a darker red-purple corolla tube, while 'R14-2x-PK1' has tall plant height, and larger red-purple flowers with a darker red-purple corolla tube. 'R14-4x-PK1' and 'R14-2x-PK1' form fruits and seeds while 'R16-1-1' does not.

When 'R16-1-1' is compared to the UF variety 'R10-105-Q54' (U.S. Plant Pat. No. 26,063), 'R16-1-1' has average plant height and width of 49 cm 51 cm, respectively, while 'R10-105-Q54' has average plant height and width of 80 cm 64 cm, respectively. Corolla diameter in 'R16-1-1' is 3.0-4.0 cm and its color is RHS 73D (red-purple) with darker RHS 72A (red-purple) tube, while corolla diameter in 'R10-105-Q54' is 4.5-5.2 cm and its color is RHS 66D (red-violet) with darker RHS 74A (red-violet) tube. When 'R10-105-Q54' is hand pollinated with pollen from wild *Ruellia simplex* or 'Chi Chi', respectively, 35% and 50% of the crosses result in fruit formation, but all fruits abort before maturation and seeds are not viable. 'R16-1-1' does not form fruits or seeds.

When 'R16-1-1' is compared to the known variety 'Chi Chi' (commercial cultivar, not patented), 'R16-1-1' has average plant height and width of 49 cm 51 cm, respectively, while 'Chi Chi' has average plant height and width of 60 cm 62 cm, respectively. Corolla diameter in 'R16-1-1' is 3.0-4.0 cm and its color is RHS 73D (red-purple) with darker RHS 72A (red-purple) tube, while corolla diameter in 'Chi Chi' is 4.8-5.4 cm and its color is RHS 68D (red-purple) with darker RHS 64C (red-purple) tube. One plant of 'Chi Chi' produces approximately 120 fruits during 60 days, and has an average of 18 seeds per fruit with 82% germination rate, resulting in about 1,770 seedlings. 'R16-1-1' does not form fruits or seeds.

We claim:

1. A new and distinct variety of *Ruellia* plant named 'R16-1-1' as illustrated and described herein.

* * * * *